United States Patent
Nakajima et al.

(10) Patent No.: US 11,246,501 B2
(45) Date of Patent: Feb. 15, 2022

(54) BIOLOGICAL INFORMATION ANALYSIS DEVICE, SYSTEM, AND PROGRAM

(71) Applicants: OMRON Corporation, Kyoto (JP); OMRON HEALTHCARE Co., Ltd., Kyoto (JP)

(72) Inventors: Hiroshi Nakajima, Kyoto (JP); Hirotaka Wada, Kyoto (JP); Naoki Tsuchiya, Otsu (JP); Masaaki Kasai, Nara (JP); Eriko Kan, Kyoto (JP); Toru Uenoyama, Kyoto (JP); Keiichi Obayashi, Tokyo (JP); Ayako Kokubo, Uji (JP); Yuya Ota, Kyoto (JP); Toshikazu Shiga, Otsu (JP); Mitsuo Kuwabara, Hirakata (JP); Hironori Sato, Moriyama (JP); Ken Miyagawa, Kyoto (JP); Masakazu Tsutsumi, Muko (JP)

(73) Assignees: Omron Corporation, Kyoto (JP); Omron Healthcare Co., Ltd., Kyoto (JP)

( * ) Notice: Subject to any disclaimer, the term of this patent is extended or adjusted under 35 U.S.C. 154(b) by 688 days.

(21) Appl. No.: 16/092,159

(22) PCT Filed: Apr. 14, 2017

(86) PCT No.: PCT/JP2017/015282
§ 371 (c)(1),
(2) Date: Oct. 8, 2018

(87) PCT Pub. No.: WO2017/179701
PCT Pub. Date: Oct. 19, 2017

(65) Prior Publication Data
US 2019/0125252 A1    May 2, 2019

(30) Foreign Application Priority Data
Apr. 15, 2016 (JP) .............................. JP2016-082463

(51) Int. Cl.
*A61B 5/02* (2006.01)
*A61B 5/029* (2006.01)
(Continued)

(52) U.S. Cl.
CPC ............ *A61B 5/029* (2013.01); *A61B 5/0002* (2013.01); *A61B 5/021* (2013.01); *A61B 5/022* (2013.01);
(Continued)

(58) Field of Classification Search
CPC ......... A61B 5/029; A61B 5/316; A61B 5/352; A61B 5/024; A61B 5/02028;
(Continued)

(56) References Cited

U.S. PATENT DOCUMENTS

| 4,365,636 A | 12/1982 | Barker |
| 5,400,793 A | 3/1995 | Wesseling |

(Continued)

FOREIGN PATENT DOCUMENTS

| CN | 1140582 A | 1/1997 |
| CN | 1158077 A | 8/1997 |

(Continued)

OTHER PUBLICATIONS

Office Action in the counterpart Japanese Patent Application No. 2018-512086 dated May 26, 2020 (8 pages).

(Continued)

*Primary Examiner* — Andrey Shostak
(74) *Attorney, Agent, or Firm* — Osha Bergman Watanabe & Burton LLP (57) ABSTRACT

A biological information analysis device including: an indicator extraction unit that is configured to extract, from time-series data regarding blood pressure waveforms consecutively measured by a sensor that is configured to be worn on a body part of a user and to be capable of (Continued)

non-invasively measuring a blood pressure waveform for each heartbeat, data regarding blood pressure waveforms corresponding to a period of time in which a change in blood pressure occurs, and extract an indicator that is related to the functionality of respiratory organs of the user, based on characteristics of the blood pressure waveforms corresponding to the period of time; and a processing unit that performs processing that is based on the indicator thus extracted.

6 Claims, 7 Drawing Sheets

(51) Int. Cl.
| | |
|---|---|
| A61B 5/08 | (2006.01) |
| A61B 5/024 | (2006.01) |
| A61B 5/316 | (2021.01) |
| A61B 5/352 | (2021.01) |
| A61B 5/022 | (2006.01) |
| A61B 5/0205 | (2006.01) |
| A61B 5/021 | (2006.01) |
| A61B 5/00 | (2006.01) |
| G16H 10/40 | (2018.01) |
| G16H 50/20 | (2018.01) |
| A61B 5/11 | (2006.01) |
| A61M 16/00 | (2006.01) |
| A61F 5/56 | (2006.01) |
| A61M 21/00 | (2006.01) |
| G06F 1/16 | (2006.01) |
| A61B 5/145 | (2006.01) |
| A61B 5/026 | (2006.01) |

(52) U.S. Cl.
CPC ............ *A61B 5/024* (2013.01); *A61B 5/0205* (2013.01); *A61B 5/02028* (2013.01); *A61B 5/02055* (2013.01); *A61B 5/02108* (2013.01); *A61B 5/02116* (2013.01); *A61B 5/02125* (2013.01); *A61B 5/02225* (2013.01); *A61B 5/02233* (2013.01); *A61B 5/02438* (2013.01); *A61B 5/08* (2013.01); *A61B 5/0816* (2013.01); *A61B 5/1118* (2013.01); *A61B 5/316* (2021.01); *A61B 5/352* (2021.01); *A61B 5/4818* (2013.01); *A61B 5/4836* (2013.01); *A61B 5/4884* (2013.01); *A61B 5/681* (2013.01); *A61B 5/6801* (2013.01); *A61B 5/6824* (2013.01); *A61B 5/721* (2013.01); *A61B 5/7221* (2013.01); *A61B 5/7239* (2013.01); *A61B 5/7275* (2013.01); *A61B 5/7278* (2013.01); *A61B 5/7282* (2013.01); *A61B 5/742* (2013.01); *A61B 5/743* (2013.01); *A61B 5/746* (2013.01); *A61F 5/56* (2013.01); *A61M 16/024* (2017.08); *A61M 21/00* (2013.01); *G06F 1/163* (2013.01); *G16H 10/40* (2018.01); *G16H 50/20* (2018.01); *A61B 5/026* (2013.01); *A61B 5/02141* (2013.01); *A61B 5/14532* (2013.01); *A61B 5/14542* (2013.01); *A61B 5/4806* (2013.01); *A61B 5/683* (2013.01); *A61B 5/7203* (2013.01); *A61B 5/7257* (2013.01); *A61B 2560/0242* (2013.01); *A61B 2562/029* (2013.01); *A61M 2021/0022* (2013.01); *A61M 2021/0027* (2013.01); *A61M 2021/0044* (2013.01); *A61M 2021/0083* (2013.01)

(58) Field of Classification Search
CPC ..... A61B 5/1118; A61B 5/4884; A61B 5/742; A61B 5/4836; A61B 5/7221; A61B 5/746; A61B 5/021; A61B 5/02233; A61B 5/4818; A61B 5/7282; A61B 5/02116; A61B 5/02438; A61B 5/6801; A61B 5/0002; A61B 5/0816; A61B 5/0205; A61B 5/02108; A61B 5/02225; A61B 5/6824; A61B 5/7239; A61B 5/02055; A61B 5/02125; A61B 5/681; A61B 5/721; A61B 5/7275; A61B 5/7278; A61B 5/743; A61B 5/08; A61B 5/022; A61B 5/14542; A61B 5/14532; A61B 2562/029; A61B 2560/0242; A61B 5/4806; A61B 5/7257; A61B 5/02141; A61B 5/683; A61B 5/7203; A61B 5/026; G06F 1/163; A61M 16/024; A61M 21/00; A61M 2021/0022; A61M 2021/0027; A61M 2021/0044; A61M 2021/0083; A61F 5/56; G16H 10/40; G16H 50/20

See application file for complete search history.

(56) References Cited

U.S. PATENT DOCUMENTS

| | | | |
|---|---|---|---|
| 5,749,366 A | 5/1998 | Odagiri et al. | |
| 5,772,601 A | 6/1998 | Oka et al. | |
| 5,836,884 A | 11/1998 | Chio | |
| 5,857,975 A | 1/1999 | Golub | |
| 5,865,756 A | 2/1999 | Peel, III | |
| 5,941,837 A | 8/1999 | Amano et al. | |
| 5,980,464 A | 11/1999 | Tsuda | |
| 6,030,342 A | 2/2000 | Amano et al. | |
| 6,042,549 A | 3/2000 | Amano et al. | |
| 6,081,742 A | 6/2000 | Amano et al. | |
| 6,091,973 A | 7/2000 | Colla et al. | |
| 6,095,984 A | 8/2000 | Amano et al. | |
| 6,126,595 A | 10/2000 | Amano et al. | |
| 6,287,262 B1 | 9/2001 | Amano et al. | |
| 6,293,915 B1 | 9/2001 | Amano et al. | |
| 6,331,159 B1 | 12/2001 | Amano et al. | |
| 6,334,850 B1 | 1/2002 | Amano et al. | |
| 6,361,501 B1 | 3/2002 | Amano et al. | |
| 6,443,906 B1 | 9/2002 | Ting et al. | |
| 6,554,763 B1 | 4/2003 | Amano et al. | |
| 6,955,648 B2 | 10/2005 | Mozayeni et al. | |
| 2002/0173726 A1 | 11/2002 | Narimatsu | |
| 2003/0000522 A1 | 1/2003 | Lynn et al. | |
| 2003/0004421 A1 | 1/2003 | Ting et al. | |
| 2003/0004423 A1* | 1/2003 | Lavie | A61B 5/1073 600/500 |
| 2003/0088184 A1 | 5/2003 | Kelly | |
| 2003/0149369 A1 | 8/2003 | Gallant et al. | |
| 2003/0163034 A1 | 8/2003 | Dekker | |
| 2003/0204143 A1 | 10/2003 | Lin | |
| 2003/0204144 A1 | 10/2003 | Lin | |
| 2004/0044276 A1 | 3/2004 | Arnold | |
| 2004/0176692 A1 | 9/2004 | Kario et al. | |
| 2004/0210143 A1 | 10/2004 | Gallant et al. | |
| 2005/0075531 A1 | 4/2005 | Loeb et al. | |
| 2005/0096557 A1 | 5/2005 | Vosburgh et al. | |
| 2005/0187480 A1 | 8/2005 | Kario et al. | |
| 2006/0036126 A1 | 2/2006 | Ross et al. | |
| 2006/0142663 A1 | 6/2006 | Sawanoi et al. | |
| 2006/0200011 A1* | 9/2006 | Suzuki | A61B 5/4812 600/301 |
| 2007/0021673 A1 | 1/2007 | Arbel et al. | |
| 2007/0118028 A1 | 5/2007 | Kitajima et al. | |
| 2007/0282227 A1 | 12/2007 | Nanba et al. | |
| 2008/0027331 A1 | 1/2008 | Suzuki et al. | |
| 2008/0064965 A1* | 3/2008 | Jay | A61B 5/411 600/484 |
| 2008/0200774 A1 | 8/2008 | Luo | |
| 2008/0262362 A1 | 10/2008 | Kolluri et al. | |
| 2008/0294021 A1 | 11/2008 | Lin et al. | |
| 2009/0124914 A1 | 5/2009 | Kuo et al. | |
| 2009/0216132 A1 | 8/2009 | Orbach | |

(56) References Cited

U.S. PATENT DOCUMENTS

| | | |
|---|---|---|
| 2009/0227425 A1 | 9/2009 | Shirasaki et al. |
| 2010/0121207 A1 | 5/2010 | Moersdorf et al. |
| 2010/0130874 A1 | 5/2010 | Joeken |
| 2010/0222650 A1 | 9/2010 | Tanishima et al. |
| 2010/0228139 A1 | 9/2010 | Nanba et al. |
| 2010/0268097 A1 | 10/2010 | Hatib et al. |
| 2010/0298721 A1 | 11/2010 | Kim et al. |
| 2011/0077534 A1 | 3/2011 | Kobayashi et al. |
| 2011/0077536 A1 | 3/2011 | Kubo |
| 2011/0098540 A1 | 4/2011 | Tanishima et al. |
| 2011/0152651 A1 | 6/2011 | Berkow |
| 2011/0166458 A1 | 7/2011 | Gallant et al. |
| 2011/0190643 A1 | 8/2011 | Zhang et al. |
| 2011/0224748 A1 | 9/2011 | Lippert et al. |
| 2011/0230729 A1 | 9/2011 | Shirasaki et al. |
| 2012/0029361 A1 | 2/2012 | Addison et al. |
| 2012/0108983 A1 | 5/2012 | Banet et al. |
| 2012/0125337 A1 | 5/2012 | Asanoi |
| 2013/0053664 A1 | 2/2013 | Jian et al. |
| 2013/0085079 A1 | 4/2013 | Gill et al. |
| 2013/0184545 A1 | 7/2013 | Blomqvist et al. |
| 2014/0018687 A1 | 1/2014 | Mano |
| 2014/0058220 A1 | 2/2014 | LeBoeuf et al. |
| 2014/0081101 A1 | 3/2014 | Shirasaki et al. |
| 2014/0163399 A1 | 6/2014 | Gallant et al. |
| 2014/0213858 A1 | 7/2014 | Presura et al. |
| 2014/0247970 A1 | 9/2014 | Taylor |
| 2014/0257124 A1 | 9/2014 | Morita |
| 2014/0275937 A1 | 9/2014 | Goedje et al. |
| 2014/0276071 A1 | 9/2014 | Hunziker et al. |
| 2014/0276123 A1 | 9/2014 | Yang |
| 2014/0303509 A1 | 10/2014 | Campbell |
| 2015/0099991 A1 | 4/2015 | Yamaguchi et al. |
| 2015/0109124 A1 | 4/2015 | He et al. |
| 2015/0164351 A1 | 6/2015 | He et al. |
| 2015/0168423 A1 | 6/2015 | Gill et al. |
| 2015/0196209 A1 | 7/2015 | Morris et al. |
| 2015/0245772 A1 | 9/2015 | Kawamoto et al. |
| 2015/0305632 A1 | 10/2015 | Najarian et al. |
| 2016/0058385 A1 | 3/2016 | Ajima |
| 2017/0209052 A1 | 7/2017 | Nakamura |
| 2017/0209074 A1 | 7/2017 | Siu et al. |
| 2017/0224227 A1 | 8/2017 | Kitagawa et al. |
| 2018/0028075 A1 | 2/2018 | Presura et al. |
| 2018/0078157 A1 | 3/2018 | Yang |
| 2018/0333056 A1 | 11/2018 | Chou |
| 2019/0083723 A1 | 3/2019 | Asanoi |
| 2020/0166523 A1 | 5/2020 | Gill et al. |

FOREIGN PATENT DOCUMENTS

| | | |
|---|---|---|
| CN | 1195277 A | 10/1998 |
| CN | 1199347 A | 11/1998 |
| CN | 1243425 A | 2/2000 |
| CN | 1430484 A | 7/2003 |
| CN | 1568158 A | 1/2005 |
| CN | 1627916 A | 6/2005 |
| CN | 1723839 A | 1/2006 |
| CN | 1785117 A | 6/2006 |
| CN | 1931088 A | 3/2007 |
| CN | 101081167 A | 12/2007 |
| CN | 101193588 A | 6/2008 |
| CN | 101288586 A | 10/2008 |
| CN | 101321490 A | 12/2008 |
| CN | 201409913 Y | 2/2010 |
| CN | 101773387 A | 7/2010 |
| CN | 101785666 A | 7/2010 |
| CN | 102038495 A | 5/2011 |
| CN | 102043893 A | 5/2011 |
| CN | 102481127 A | 5/2012 |
| CN | 102697506 A | 10/2012 |
| CN | 103126655 A | 6/2013 |
| CN | 103230267 A | 8/2013 |
| CN | 103230268 A | 8/2013 |
| CN | 103781414 A | 5/2014 |
| CN | 103959060 A | 7/2014 |
| CN | 104055496 A | 9/2014 |
| CN | 104138253 A | 11/2014 |
| CN | 104188639 A | 12/2014 |
| CN | 104352228 A | 2/2015 |
| CN | 104382569 A | 3/2015 |
| CN | 104511150 A | 4/2015 |
| CN | 104665799 A | 6/2015 |
| CN | 104665821 A | 6/2015 |
| CN | 104856661 A | 8/2015 |
| CN | 104873182 A | 9/2015 |
| CN | 204618202 U | 9/2015 |
| CN | 104958064 A | 10/2015 |
| CN | 204708829 U | 10/2015 |
| CN | 105030195 A | 11/2015 |
| CN | 105054918 A | 11/2015 |
| CN | 105078474 A | 11/2015 |
| CN | 204909471 U | 12/2015 |
| CN | 105266828 A | 1/2016 |
| CN | 105361858 A | 3/2016 |
| CN | 105377124 A | 3/2016 |
| CN | 105455797 A | 4/2016 |
| DE | 10243265 A1 | 3/2004 |
| EP | 0872255 A1 | 10/1998 |
| EP | 0875199 A1 | 11/1998 |
| EP | 1057450 A2 | 12/2000 |
| EP | 1150604 A1 | 11/2001 |
| EP | 1334693 A1 | 8/2003 |
| EP | 2759257 A1 | 7/2014 |
| JP | H06-142082 A | 5/1994 |
| JP | H08-229011 A | 9/1996 |
| JP | H08-229012 A | 9/1996 |
| JP | H08-317912 A | 12/1996 |
| JP | H09-220207 A | 8/1997 |
| JP | H10-185639 A | 7/1998 |
| JP | H11-033003 A | 2/1999 |
| JP | H11-128186 A | 5/1999 |
| JP | 2002-224059 A | 8/2002 |
| JP | 2002-536104 A | 10/2002 |
| JP | 2002336210 A | 11/2002 |
| JP | 2003-24310 A | 1/2003 |
| JP | 2003-325465 A | 11/2003 |
| JP | 2004-121865 A | 4/2004 |
| JP | 2004-136105 A | 5/2004 |
| JP | 2004-223271 A | 8/2004 |
| JP | 2004-261452 A | 9/2004 |
| JP | 2005-21619 A | 1/2005 |
| JP | 2005-237472 A | 9/2005 |
| JP | 2005-532111 A | 10/2005 |
| JP | 2006-212218 A | 8/2006 |
| JP | 3820719 B2 | 9/2006 |
| JP | 2007-117591 A | 5/2007 |
| JP | 2008-61824 A | 3/2008 |
| JP | 2008-086568 A | 4/2008 |
| JP | 2008-536545 A | 9/2008 |
| JP | 2010-22689 A | 2/2010 |
| JP | 2010-200901 A | 9/2010 |
| JP | 2011-189080 A | 9/2011 |
| JP | 2012-521223 A | 9/2012 |
| JP | 2012-205673 A | 10/2012 |
| JP | 2013-31568 A | 2/2013 |
| JP | 2013-094222 A | 5/2013 |
| JP | 2013-517908 A | 5/2013 |
| JP | 2013-208140 A | 10/2013 |
| JP | 2014-105 A | 1/2014 |
| JP | 2014-14556 A | 1/2014 |
| JP | 2014000458 A | 1/2014 |
| JP | 2014-18272 A | 2/2014 |
| JP | 2014-171589 A | 9/2014 |
| JP | 2015-100525 A | 6/2015 |
| JP | 2016002119 A | 1/2016 |
| JP | 2016-87003 A | 5/2016 |
| JP | 2017-189511 A | 10/2017 |
| WO | 97/38626 A1 | 10/1997 |
| WO | 99/26529 A1 | 6/1999 |
| WO | 2004/004558 A1 | 1/2004 |
| WO | 2008/001607 A1 | 1/2008 |
| WO | 2009/020114 A1 | 2/2009 |
| WO | 2009/076126 A1 | 6/2009 |

(56) References Cited

FOREIGN PATENT DOCUMENTS

| WO | 2014/171465 A1 | 10/2014 |
|---|---|---|
| WO | 2015/178439 A2 | 11/2015 |
| WO | 2016/017579 A1 | 2/2016 |
| WO | 2016/018906 A1 | 2/2016 |
| WO | 2018/017425 A1 | 1/2018 |

OTHER PUBLICATIONS

Du Jun, "Blood pressure changes and heart rate variability in sleep apnea at night", Foreign Medical Neurology Neurosurgery, vol. 24, No. 5,1997, pp. 271-272 (2 pages).
Office Action issued in Chinese Application No. 201780022781.6; dated Jul. 13, 2020 (17 pages).
Office Action issued in Chinese Application No. 201780022529.5; dated Jul. 17, 2020 (20 pages).
Office Action issued in Chinese Application No. 201780022536.5; dated Jul. 27, 2020 (23 pages).
Office Action issued in Chinese Application No. 201780022567.0; dated Jul. 28, 2020 (20 pages).
Notice of Reasons for Refusal issued in Japanese Application No. 2018-512086, dated Feb. 24, 2020 (5 pages).
Office Action issued in Chinese Application No. 201780022537.X, dated Feb. 25, 2021 (18 pages).
Office Action issued in Chinese Application No. 201780022567.0, dated Mar. 1, 2021 (16 pages).
Office Action issued in Chinese Application No. 201780022528.0, dated Mar. 2, 2021 (10 pages).
Yigang et al.; "Ventricular Arrhythmias;" Shanghai Jiao Tong University; pp. 258-262 (9 pages).
Guo Dong, Wang Weihua, Li Qingmin, "Three-Hypers" and cardiocerebrovascular disease (M). 2014 (4 pages).
Extended European Search Report issued in Application No. 17782512. 2, dated Jan. 21, 2020 (8 pages).
Office Action issued in Chinese Application No. 201780022565.1; dated Sep. 1, 2020 (25 pages).
Office Action issued in Chinese Application No. 201780022527.6; dated Oct. 10, 2020 (17 pages).
Office Action issued in U.S. Appl. No. 16/092,151; dated Oct. 19, 2020 (18 pages).
International Search Report issued in Application No. PCT/JP2017/015274, dated Jun. 20, 2017 (2 pages).
Written Opinion issued in International Application No. PCT/JP2017/015274, dated Jun. 20, 2017, (5 pages).
International Preliminary Report on Patentability issued in Application No. PCT/JP2017/015274, dated Oct. 16, 2018 (6 pages).
International Search Report issued in Application No. PCT/JP2017/015275, dated Jul. 4, 2017 (2 pages).
Written Opinion issued in International Application No. PCT/JP2017/015275, dated Jul. 4, 2017 (7 pages).
International Preliminary Report on Patentability issued in Application No. PCT/JP2017/015275, dated Oct. 16, 2018 (8 pages).
International Search Report issued in Application No. PCT/JP2017/015276, dated Jun. 27, 2017 (2 pages).
Written Opinion issued in International Application No. PCT/JP2017/015276, dated Jun. 27, 2017 (4 pages).
International Preliminary Report on Patentability issued in Application No. PCT/JP2017/015276, dated Oct. 16, 2018 (5 pages).
International Search Report issued in Application No. PCT/JP2017/015277, dated Jul. 18, 2017 (2 pages).
Written Opinion issued in International Application No. PCT/JP2017/015277, dated Jul. 18, 2017 (4 pages).
International Preliminary Report on Patentability issued in Application No. PCT/JP2017/015277, dated Oct. 16, 2018 (5 pages).
International Search Report issued in Application No. PCT/JP2017/015278, dated Jul. 11, 2017 (2 pages).
Written Opinion issued in International Application No. PCT/JP2017/015278, dated Jul. 11, 2017 (4 pages).
International Preliminary Report on Patentability issued in Application No. PCT/JP2017/015278, dated Oct. 16, 2018 (5 pages).
International Search Report issued in Application No. PCT/JP2017/015279, dated Jul. 11, 2017 (1 page).
Written Opinion issued in International Application No. PCT/JP2017/015279, dated Jul. 11, 2017 (4 pages).
International Preliminary Report on Patentability issued in Application No. PCT/JP2017/015279, dated Oct. 16, 2018 (5 pages).
International Search Report issued in Application No. PCT/JP2017/015280, dated Jul. 18, 2017 (2 pages).
Written Opinion issued in International Application No. PCT/JP2017/015280, dated Jul. 18, 2017 (4 pages).
International Preliminary Report on Patentability issued in Application No. PCT/JP2017/015280, dated Oct. 16, 2018 (5 pages).
International Search Report issued in Application No. PCT/JP2017/015281, dated Jul. 18, 2017 (2 pages).
Written Opinion issued in International Application No. PCT/JP2017/015281, dated Jul. 18, 2017 (3 pages).
International Preliminary Report on Patentability issued in Application No. PCT/JP2017/015281, dated Oct. 16, 2018 (4 pages).
International Search Report issued in Application No. PCT/JP2017/015282, dated Jul. 11, 2017 (1 page).
Written Opinion issued in International Application No. PCT/JP2017/015282, dated Jul. 11, 2017 (3 pages).
International Preliminary Report on Patentability issued in Application No. PCT/JP2017/015282, dated Oct. 16, 2018 (4 pages).
International Search Report issued in Application No. PCT/JP2017/015283, dated Jul. 11, 2017 (1 page).
Written Opinion issued in International Application No. PCT/JP2017/015283, dated Jul. 11, 2017 (3 pages).
International Preliminary Report on Patentability issued in Application No. PCT/JP2017/015283, dated Oct. 16, 2018 (4 pages).
International Search Report issued in Application No. PCT/JP2017/015284, dated Jun. 27, 2017 (2 pages).
Written Opinion issued in International Application No. PCT/JP2017/015284, dated Jun. 27, 2017 (3 pages).
International Preliminary Report on Patentability issued in Application No. PCT/JP2017/015284, dated Oct. 16, 2018 (4 pages).
Office Action issued in the counterpart U.S. Appl. No. 16/092,151, dated Mar. 30, 2020 (29 pages).
Office Action issued in U.S. Appl. No. 16/092,060, dated Mar. 25, 2021 (50 pages).
McGee; "Evidence-Based Physical Diagnosis;" ScienceDirect; 4th Edition; 2017 (4 pages).
Office Action issued in Chinese Application No. 201780022529.5; dated Jan. 5, 2021 (19 pages).
Office Action issued in Chinese Application No. 201780022566.6; dated Aug. 4, 2020 (19 pages).
Office Action issued in Chinese Application No. 201780022528.0; dated Aug. 31, 2020 (19 pages).
Office Action issued in Chinese Application No. 201780022530.8; dated Oct. 9, 2020 (16 pages).
Office Action issued in Chinese Application No. 201780022568.5; dated Oct. 10, 2020 (22 pages).
Office Action issued in Japanese Application No. 2018-512086; dated Oct. 6, 2020 (5 pages).
P. Boudreau et al. "Circadian Variation of Heart Rate Variability Across Sleep Stages" SLEEP, vol. 36, No. 12, 2013 (10 pages).
Q. Han et al. "The Method of Simultaneously Removing Breathing Baseline and High-frequency Noise in Pulse Wave Signal" Chinese Journal of Medical Physics, vol. 31, No. 2 (5 pages).
Extended European Search Report issued in Application No. 17782508. 0, dated Sep. 30, 2019 (8 pages).
Extended European Search Report issued in Application No. 17782507. 2, dated Sep. 30, 2019 (8 pages).
Extended European Search Report issued in Application No. 17782506. 4, dated Oct. 29, 2019 (9 pages).
Extended European Search Report issued in Application No. 17782509. 8, dated Nov. 4, 2019 (8 pages).
Extended European Search Report issued in Application No. 17782514. 8, dated Nov. 4, 2019 (9 pages).
Extended European Search Report issued in Application No. 17782515. 5, dated Nov. 7, 2019 (9 pages).

(56) References Cited

OTHER PUBLICATIONS

Extended European Search Report issued in Application No. 17782510.6, dated Nov. 7, 2019 (9 pages).
Extended European Search Report issued in Application No. 17782511.4, dated Nov. 7, 2019 (9 pages).
Extended European Search Report issued in Application No. 17782513.0, dated Nov. 13, 2019 (8 pages).
Extended European Search Report issued in Application No. 17782516.3, dated Nov. 12, 2019 (8 pages).
Office Action issued in U.S. Appl. No. 16/092,095; dated Jul. 26, 2021 (66 pages).
Office Action issued in U.S. Appl. No. 16/092,167; dated Aug. 3, 2021 (88 pages).
Office Action issued in U.S. Appl. No. 16/092,113; dated Aug. 4, 2021 (94 pages).
W. Hu et al. "Diastolic Blood Pressure Rises with the Exacerbation of Obstructive Sleep Apnea in Males" Obesity, vol. 25, No. 11; Nov. 2017 (9 pages).
Office Action issued in U.S. Appl. No. 16/092,134; dated Jun. 23, 2021 (84 pages).
Office Action issued in U.S. Appl. No. 16/092,076; dated Jun. 28, 2021 (78 pages).
Office Action issued in U.S. Appl. No. 16/092,060; dated Jul. 9, 2021 (30 pages).
Restriction Requirement issued in U.S. Appl. No. 16/092,136; dated Jul. 12, 2021 (7 pages).

\* cited by examiner

RESULTS OF ANALYSIS OF BLOOD PRESSURE
WAVEFORM ON 2015/11/9

SURGES CAUSED BY APNEA :   TEN TIMES/DAY
  MAXIMUM AMOUNT OF CHANGE :    x x x
  AVERAGE AMOUNT OF CHANGE :    x x x
  VARIATION IN AMOUNT OF CHANGE : x x x

SURGES CAUSED BY ANOTHER FACTOR :   THREE TIMES/DAY
  MAXIMUM AMOUNT OF CHANGE :    x x x
  AVERAGE AMOUNT OF CHANGE :    x x x
  VARIATION IN AMOUNT OF CHANGE : x x x

MESSAGE :

BE CAREFUL
MANY SURGES HAVE BEEN
CAUSED BY APNEA.

BIOLOGICAL INFORMATION ANALYSIS DEVICE, SYSTEM, AND PROGRAM

TECHNICAL FIELD

The present invention relates to technology for acquiring useful information from a blood pressure waveform that has been measured.

RELATED ART

There is a known technology for measuring changes in the internal pressure of a radial artery and recording the shape of a pressure pulse wave (blood pressure waveform). Patent Document 1 (JP 2008-61824A) discloses that a blood pressure waveform is measured using a tonometry method, and pieces of information such as an AI (Augmentation Index) value, a pulse wave period, a baseline fluctuation rate, sharpness, and an ET (Ejection Time) are acquired from the blood pressure waveform. Also, Patent Document 2 (JP 2005-532111A) discloses that a blood pressure waveform is measured using a wristwatch-type blood pressure meter, in which a mean arterial pressure, a mean systolic pressure, a mean diastolic pressure, a mean systolic pressure indicator, and a mean diastolic pressure indicator are calculated from the blood pressure waveform, and an alert is output when any of these values deviates from a reference value.

RELATED ART DOCUMENTS

Patent Documents

Patent Document 1: JP 2008-61824A
Patent Document 2: JP 2005-532111A

SUMMARY OF THE INVENTION

Problem to be Solved by the Invention

Conventionally, in order to acquire information regarding respiratory organs, it is necessary to attach a dedicated sensor such as a flow sensor to a body part, which places great physical or psychological burden on the user. Therefore, if it is possible to acquire information regarding respiratory organs by using a simple method that places less burden on the user, such a method would be very useful.

The inventors of the present invention have been worked hard to develop a blood pressure measurement device that can accurately measure an ambulatory blood pressure waveform for each heartbeat, and to put such a device into practical use. Through experiments performed on subjects during the development phase, the inventors have found that various kinds of useful information can be extracted from data regarding ambulatory blood pressure waveforms that have been consecutively measured. For example, although conventional blood pressure meters can only acquire information regarding blood pressure, it has become more apparent that, for example, information regarding respiratory organs can also be extracted in addition to information related to blood pressure, by accurately and non-invasively monitoring ambulatory blood pressure waveforms taken every heartbeat.

The present invention aims to provide a novel technology for extracting information related to respiratory organs from time-series data regarding blood pressure waveforms.

Means for Solving the Problems

To achieve the above-described aim, the present invention employs the following configurations.

A biological information analysis device according to the present invention is a biological information analysis device that includes: an indicator extraction unit that is configured to extract, from time-series data regarding blood pressure waveforms consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, and extract an indicator related to the functionality of respiratory organs of the user, based on characteristics of the blood pressure waveforms corresponding to the period of time; and a processing unit that performs processing that is based on the indicator thus extracted.

The inventors of the present invention have found that a temporal increase in systolic blood pressure (a surge in blood pressure) occurs if apnea occurs. Therefore, it is possible to extract information related to the functionality of respiratory organs, such as the occurrence of apnea, by focusing on characteristics of a blood pressure waveform in a period of time in which a change in blood pressure has occurred, as with the present invention. With this configuration, it is possible to acquire information related to the functionality of respiratory organs by simply analyzing time-series data regarding a blood pressure waveform, which is very easy and advantageous.

A change in blood pressure is not only caused by apnea, but also by other various factors. Therefore, it is preferable that the indicator extraction unit is configured to determine whether or not a cause of a change in blood pressure in the period of time is apnea, based on the characteristics of the blood pressure waveforms corresponding to the period of time. With this configuration, it is possible to determine whether or not the cause of a change in blood pressure is apnea simply only analyzing time-series data regarding blood pressure waveforms, which is convenient. Also, by discerning between a change in blood pressure caused by apnea and a change in blood pressure caused by another factor, it is possible to calculate an indicator related to the functionality of respiratory organs with high reliability.

For example, it is preferable that the indicator extraction unit is configured to determine whether or not a cause of a change in blood pressure in the period of time is apnea, based on a relationship between: an increase and a decrease in a heart rate; and an increase and a decrease in systolic blood pressure, using the data regarding the blood pressure waveforms corresponding to the period of time. This is because both the heart rate and the systolic blood pressure increase in the case of apnea, whereas one of the heart rate and the systolic blood pressure increases, and the other decreases in cases of other factors.

The indicator extraction unit may be configured to calculate a heart rate and a systolic blood pressure value for each of the blood pressure waveforms included in the period of time, using the data regarding the blood pressure waveforms corresponding to the period of time, and determine that a cause of a change in blood pressure in the period of time is apnea when the number or proportion of blood pressure waveforms in which both the heart rate and the systolic blood pressure value are greater than a predetermined determination condition is greater than a predetermined threshold value. According to a method using such a determination condition and a threshold value, it is possible to determine a cause of a change in blood pressure, using a simple determination logic.

The indicator extraction unit may be configured to calculate, a frequency of occurrence of changes in blood pressure caused by apnea, the amount and/or statistics of the amount of changes in blood pressure caused by apnea, and so on, as the indicator related to the functionality of respiratory organs.

It is preferable that the processing unit is configured to output information related to the functionality of respiratory organs of the user, based on the indicator thus extracted.

Note that the present invention can be interpreted as a biological information analysis device or system that is provided with at least one of the above-described configurations or at least one of the above-described functions. The present invention can also be interpreted as a biological information analysis method that includes at least part of the above-described processing, or a program that causes a computer to execute such a method, or a computer-readable recording medium on which such a program is recorded in a non-transitory manner. The present invention can be formed by combining the above-described configurations and the above-described kinds of processing with each other unless no technical inconsistency occurs.

Effects of the Invention

According to the present invention, it is possible to easily presume the cause of a surge in blood pressure, based on time-series data regarding blood pressure waveforms.

EMBODIMENTS OF THE INVENTION

The following describes a preferred embodiment of the present invention with reference to the drawings. Note that the following descriptions of components may be modified as appropriate depending on the configuration of a device to which the present invention is applied, and on various conditions, and the scope of the present invention is not intended to be limited to the following descriptions.

Biological Information Analysis System

Figure 1:
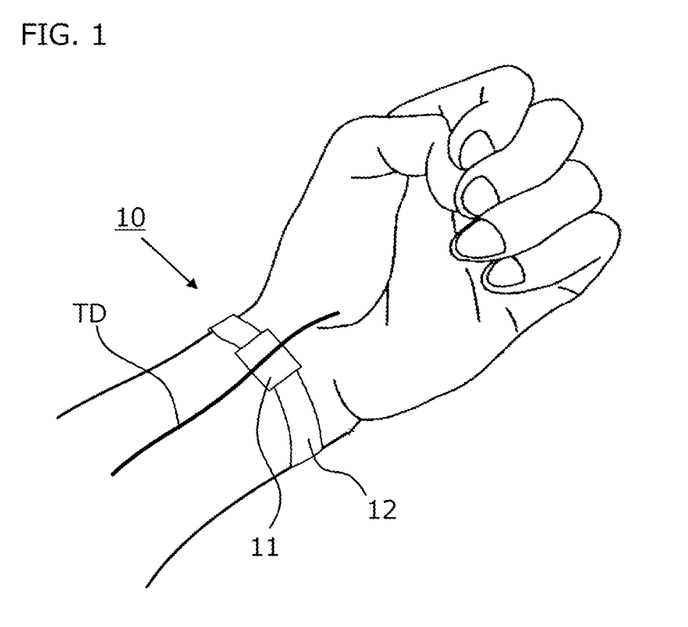
FIG. 1 shows a schematic external configuration of a biological information analysis system 10.

FIG. 1 shows a schematic external configuration of a biological information analysis system 10 according to an embodiment of the present invention. FIG. 1 shows a state in which the biological information analysis system 10 is worn on the left wrist. The biological information analysis system 10 includes a main body 11 and a belt 12 that is fixed to the main body 11. The biological information analysis system 10 is a so-called wearable device, and is worn such that the main body 11 is in contact with the skin on the palm side of the wrist, and the main body 11 is located over a radial artery TD that lies beneath the skin. Although the device is configured to be worn on the radial artery TD in the present embodiment, the device may be configured to be worn on another superficial artery.

Figure 2:
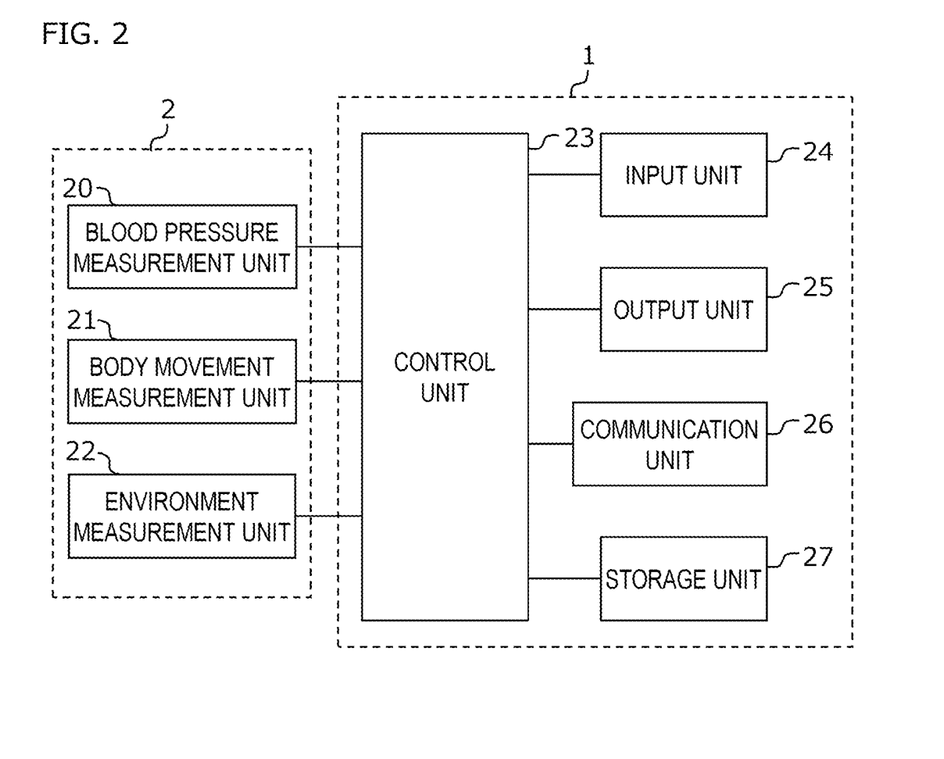
FIG. 2 is a block diagram showing a hardware configuration of the biological information analysis system 10.

FIG. 2 is a block diagram showing a hardware configuration of the biological information analysis system 10. In general, the biological information analysis system 10 includes a measurement unit 2 and the biological information analysis device 1. The measurement unit 2 is a device that performs measurement to acquire information that is used to analyze biological information, and includes a blood pressure measurement unit 20, a body movement measurement unit 21, and an environment measurement unit 22. However, note that the configuration of the measurement unit 2 is not limited to that shown in FIG. 2. For example, a unit that measures biological information other than blood pressure or a body movement (e.g. body temperature, blood-sugar level, or brain waves) may be added. Also, any unit that is not used in the example described below is not an essential component, and may be omitted from the biological information analysis system 10. The biological information analysis device 1 is a device that analyzes biological information based on information acquired from the measurement unit 2, and includes a control unit 23, an input unit 24, an output unit 25, a communication unit 26, and a storage unit 27. The units 20 to 27 are connected to each other so that signals can be exchanged between them via a local bus or other signal lines. The biological information analysis system 10 also includes a power supply (a battery), which is not shown.

The blood pressure measurement unit 20 measures a pressure pulse wave from the radial artery TD by using a tonometry method. The tonometry method is for forming a flat area in the artery TD by pressing the artery from the skin with appropriate pressure, adjusting the balance between the internal pressure and the external pressure of the artery, and non-invasively measuring the pressure pulse wave using a pressure sensor.

The body movement measurement unit 21 includes a tri-axis acceleration sensor, and measures the movement of the user's body (body movement) using this sensor. The body movement measurement unit 21 may include a circuit that converts the format of an output from the tri-axis acceleration sensor into a format that is readable to the control unit 23.

The environment measurement unit 22 measures environmental information that may affect mental and physical conditions of the user (in particular the blood pressure). The environment measurement unit 22 may include, for example, an atmospheric temperature sensor, a humidity sensor, an illuminance sensor, an altitude sensor, a position sensor, and so on. The environment measurement unit 22 may include a circuit that converts the format of outputs from these sensors and so on into a format that is readable to the control unit 23.

The control unit 23 performs various kinds of processing, such as controlling each unit of the biological information analysis system 10, acquiring data from the measurement unit 2, storing the acquired data in the storage unit 27, processing and analyzing data, and inputting and outputting data. The control unit 23 includes a hardware processor (hereinafter referred to as the "CPU") a ROM (Read Only Memory), a RAM (Random Access Memory), and so on. Processing that is performed by the control unit 23, which will be described later, is realized by the CPU reading and executing a program stored in the ROM or the storage unit 27. The RAM functions as a work memory that is used by the control unit 23 when performing various kinds of processing. Although acquisition of data from the measurement unit 2 and the storing of data in the storage unit 27 are performed by the control unit 23 in the present embodiment, it is possible to employ a configuration in which the measurement unit 2 directly stores (writes) data in the storage unit 27.

Each of the constituent components of the embodiment such as a measurement unit, an indicator extraction unit, a processing unit, a determination unit, a risk database, an input unit, an output unit, a case database, and so on may be implemented as pieces of hardware in the biological information analysis system 10. The indicator extraction unit, the processing unit, and the determination unit may receive an executable program stored in the storage unit 27, and execute the program. The indicator extraction unit, the processing unit, and the determination unit may receive data from the blood pressure measurement unit 20, the body movement measurement unit 21, the environment measurement unit 22, the input unit 24, the output unit 25, the communication unit 26, the storage unit 27, and so on as required. Databases such as the risk database and the case database may be implemented using the storage unit 27 and so on, and store pieces of information that are arranged such that a data search and data accumulation can be easily performed. Here, for example, the configuration, operations, and so on of the biological information analysis system 10 are disclosed in JP 2016-082069A. The contents of this disclosure are incorporated herein by reference. Also, the configuration, operations, and so on of the blood pressure measurement unit are disclosed in JP 2016-087003A. The contents of this disclosure are incorporated herein by reference.

The input unit 24 provides an operation interface for the user. For example, an operation button, a switch, a touch panel, and so on may be used.

The output unit 25 provides an interface that outputs information to the user. For example, a display device (such as a liquid crystal display) that outputs information using images, an audio output device or a beeper that outputs information using audio, an LED that outputs information by blinking, a vibration device that outputs information by vibrating, and so on may be used.

The communication unit 26 performs data communication with another device. Any data communication method such as a wireless LAN or Bluetooth (registered trademark) may be used.

The storage unit 27 is a storage medium that can store data and from which data can be read out, and stores programs that are to be executed by the control unit 23, pieces of measurement data acquired from the measurement units, and various kinds of data acquired by processing the pieces of measurement data, and so on. The storage unit 27 is a medium that accumulates pieces of information that are to be stored, through an electrical, magnetic, optical, mechanical, or chemical action. For example, a flash memory is used. The storage unit 27 may be a portable unit such as a memory card, or built into the biological information analysis system 10.

At least one unit or all units out of the body movement measurement unit 21, environment measurement unit 22, the control unit 23, the input unit 24, the output unit 25, and the storage unit 27 may be configured as a device that is separate from the main body 11. That is, as long as the blood pressure measurement unit 20 and the main body 11 that incorporates a circuit that controls the blood pressure measurement unit 20 are configured to be wearable on a wrist, the configurations of other units can be freely designed. If this is the case, the main body 11 cooperates with another unit via the communication unit 26. Various configurations can be conceived of. For example, the functions of the control unit 23, the input unit 24, and the output unit 25 may be realized using a smartphone application, and required data may be acquired from an activity monitor that has the functions of the body movement measurement unit 21 and the environment measurement unit 22. Also, a sensor that measures biological information other than blood pressure may be provided. For example, a sleep sensor, a blood-sugar level sensor, and the like may be combined.

Although the sensor (the blood pressure measurement unit 20) that measures blood pressure and the component (including the control unit 23 and so on) that performs processing to analyze blood pressure waveform data are provided in one device in the present embodiment, they may be provided in separate members. In the present embodiment, the component (including the control unit 23 and so on) that performs processing to analyze biological information is referred to as a biological information analysis device, and the device that includes the combination of the measurement unit and the biological information analysis device is referred to as a biological information analysis system. However, these names are given for descriptive purposes, and the measurement unit and the component that performs processing to analyze biological information may be referred to as a biological information analysis device as a whole, or other names may be used.

Measurement of Blood Pressure Waveform

Figure 3:
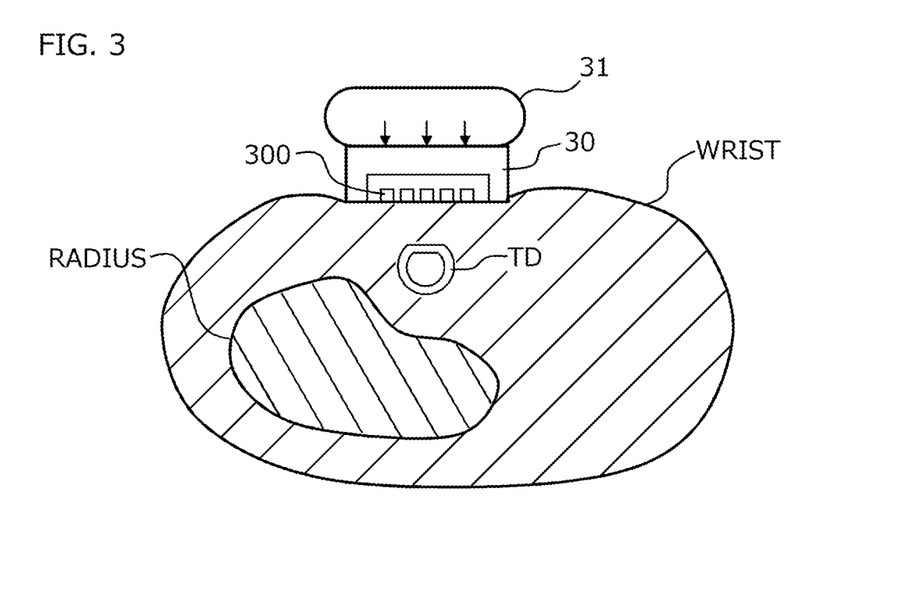
FIG. 3 is a cross-sectional view schematically showing a configuration of a blood pressure measurement unit 20 and a state in which measurement is performed.

FIG. 3 is a cross-sectional view schematically showing the configuration of the blood pressure measurement unit 20 and a state in which measurement is performed. The blood pressure measurement unit 20 includes a pressure sensor 30 and a pressurizing mechanism 31 for pressing the pressure sensor 30 against a wrist. The pressure sensor 30 includes a plurality of pressure detection elements 300. The pressure detection elements 300 are piezoelectric elements that detect pressure and convert the pressure into an electrical signal. For example, elements that utilize a piezoresistive effect may be preferably used. The pressurizing mechanism 31 includes, for example, an air bag and a pump that adjusts the internal pressure of the air bag. As a result of the control unit 23 controlling the pump to increase the internal pressure of the air bag, the air bag expands and the pressure sensor 30 is pressed against the surface of the skin. Note that the pressurizing mechanism 31 may be any mechanism as long as it can adjust the pressing force of the pressure sensor 30 applied to the surface of the skin, and is not limited to a mechanism that uses an air bag.

Upon the biological information analysis system 10 being worn on a wrist and activated, the control unit 23 controls the pressurizing mechanism 31 of the blood pressure measurement unit 20 to keep the pressing force of the pressure sensor 30 in an appropriate state (a tonometry state). Then, pressure signals detected by the pressure sensor 30 are sequentially acquired by the control unit 23. Pressure signals acquired from the pressure sensor 30 are generated by digitizing analogue physical amounts (e.g. voltage values) output by the pressure detection elements 300, through an A/D converter circuit or the like that employs a well-known technology. Preferable analogue values such as current values or resistance values may be employed as the analogue physical amounts, depending on the type of the pressure detection elements 300. Signal processing such as the aforementioned A/D conversion may be performed using a predetermined circuit provided in the blood pressure measurement unit 20, or performed by another unit (not shown) provided between the blood pressure measurement unit 20 and the control unit 23. Each pressure signal acquired by the control unit 23 corresponds to an instantaneous value of the internal pressure of the radial artery TD. Therefore, it is possible to acquire time-series data regarding blood pressure waveforms by acquiring pressure signals with time granularity and continuity that make it possible to ascertain a blood pressure waveform for each heartbeat. The control unit 23 stores the pressure signals sequentially acquired from the pressure sensor 30, in the storage unit 27, together with information regarding points in time at which the pressure signals were measured. The control unit 23 may store the acquired pressure signals in the storage unit 27 without change, or store the pressure signals in the storage unit 27 after performing required signal processing on the pressure signals. Required signal processing includes, for example, processing that is performed to calibrate each pressure signal such that the amplitude of the pressure signal matches the blood pressure value (e.g. the brachial blood pressure), processing that is performed to reduce or remove noise in each pressure signal, and so on.

Figure 4:
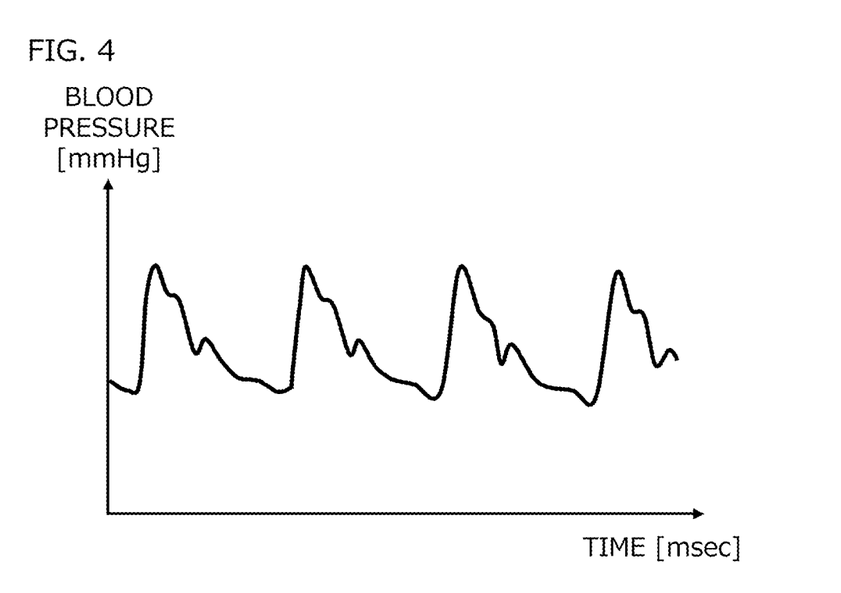
FIG. 4 shows a blood pressure waveform that is measured by the blood pressure measurement unit 20.

FIG. 4 shows a blood pressure waveform measured by the blood pressure measurement unit 20. The horizontal axis indicates time and the vertical axis indicates blood pressure. Although the sampling frequency may be set to any value, it is preferably set to be no less than 100 Hz so that characteristics of the shape of a waveform corresponding to one heartbeat can be reproduced. Typically, the period of one heartbeat is approximately one second, and therefore approximately one hundred or more data points can be acquired on a waveform corresponding to one heartbeat.

The blood pressure measurement unit 20 according to the present embodiment is advantageous in terms of the following.

The blood pressure measurement unit 20 can measure a blood pressure waveform for each heartbeat. As a result, it is possible to acquire various indicators related to blood pressure, the state of the heart, cardiovascular risks, and so on, based on the characteristics of the shape of the blood pressure waveform. In addition, it is possible to monitor for instantaneous values of blood pressure. Therefore, it is possible to instantaneously detect a blood pressure surge (a sudden rise in the blood pressure value), and to detect changes in blood pressure and irregularities in a blood pressure waveform that may occur in a very short period of time (corresponding to one to several heartbeats) without missing them.

As a portable blood pressure meter, a blood pressure meter that is to be worn on a wrist or an upper arm and employs an oscillometric method to measure blood pressure has come into practical use. However, a conventional portable blood pressure meter can only measure the mean value of blood pressure based on changes in the internal pressure of a cuff during a period of several seconds to a dozen or so seconds corresponding to a plurality of heartbeats, and cannot acquire time-series data regarding a blood pressure waveform for each heartbeat, unlike the blood pressure measurement unit 20 according to the present embodiment.

The blood pressure measurement unit 20 can record time-series data regarding blood pressure waveforms. By acquiring time-series data regarding blood pressure waveforms, and, for example, discerning characteristics of the blood pressure waveform related to temporal changes, or performing a frequency analysis on the time-series data to extract a specific frequency component, it is possible to acquire various indicators related to blood pressure, the state of the heart, cardiovascular risks, and so on.

The device employs a portable (wearable) type configuration, and less burden is placed on the user during measurement. Therefore, continuous measurement for a long time, and even 24-hour blood pressure monitoring, can be relatively easily performed. Also, since the device is of a portable type, changes in not only blood pressure under resting conditions, but also an ambulatory blood pressure (for example, during daily life or exercise) can be measured. As a result, it is possible to grasp how blood pressure is affected by behaviours in daily life (such as sleeping, eating, commuting, working, and taking medicine) and exercise, for example.

Conventional products are types of devices that measure blood pressure under resting conditions, with an arm or a wrist fixed to a blood pressure measurement unit, and cannot measure changes in blood pressure in daily life or during exercise, unlike the biological information analysis system 10 according to the present embodiment.

The blood pressure measurement unit 20 can be easily combined or linked with other sensors. For example, it is possible to make an evaluation of a cause-effect relationship or a composite evaluation with information that can be acquired by other sensors (e.g. a body movement, environmental information such as an atmospheric temperature, biological information such as SpO2 and respiration information).

Biological Information Analysis Device

Figure 5:
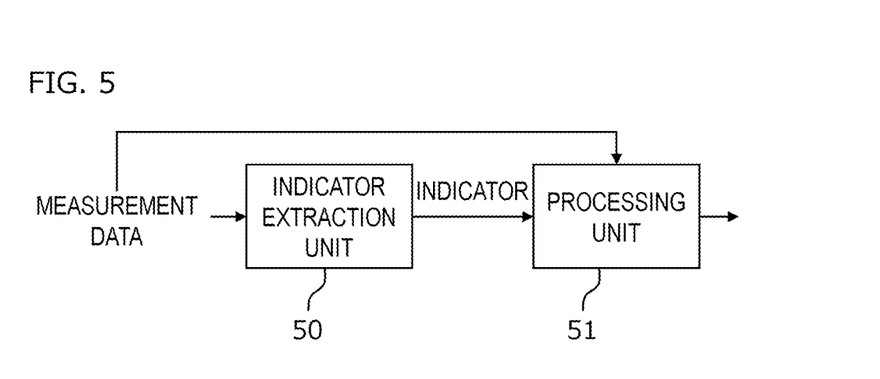
FIG. 5 is a block diagram illustrating processing that is performed by a biological information analysis device 1.

FIG. 5 is a block diagram illustrating processing that is performed by the biological information analysis device 1. As shown in FIG. 5, the biological information analysis device 1 includes an indicator extraction unit 50 and a processing unit 51. In the present embodiment, processing performed by the indicator extraction unit 50 and the processing unit 51 may be realized by the control unit 23 executing a program that is required for the processing. The program may be stored in the storage unit 27. When the control unit 23 executes the required program, the subject program stored in the ROM or storage unit 27 is loaded to the RAM. Then, the control unit 23 interprets and executes the program loaded to the RAM, using the CPU, to control each constituent component. Note that at least one or all of the processing procedures executed by the indicator extraction unit 50 and the processing unit 51 may be realized using a circuit such as an ASIC or an FPGA. Alternatively, at least one or all of the processing procedures executed by the indicator extraction unit 50 and the processing unit 51 may be realized using a computer (e.g. a smartphone, a tablet terminal, a personal computer, or a cloud server) that is separate from the main body 11.

The indicator extraction unit 50 acquires time-series data regarding blood pressure waveforms, which have been consecutively measured by the blood pressure measurement unit 20, from the storage unit 27. The indicator extraction unit 50 extracts, from the acquired time-series data regarding blood pressure waveforms, indicators that are related to characteristics of the blood pressure waveforms. Here, characteristics of a blood pressure waveform include, for example, characteristics of the shape of a blood pressure waveform corresponding to one heartbeat, temporal changes in a blood pressure waveform, and frequency components of a blood pressure waveform. However, characteristics of a blood pressure waveform are not limited to those listed above. The extracted indicators are output to the processing unit 51. There are various characteristics and indicators regarding a blood pressure waveform, and the characteristics and indicators that are to be extracted may be designed or selected as appropriate according to the purpose of processing that is to be performed by the processing unit 51. Characteristics and indicators that can be extracted from measurement data regarding blood pressure waveforms according to the present embodiment will be described later in detail.

When obtaining indicators, the indicator extraction unit 50 may use measurement data that has been acquired by the body movement measurement unit 21 and/or measurement data that has been acquired by the environment measurement unit 22, in addition to measurement data regarding blood pressure waveforms. Also, although not shown in the drawings, pieces of measurement data that have been acquired by a sleep sensor, a blood-sugar level sensor, and the like may be combined with one another. By performing complex analysis on a plurality of kinds of measurement data acquired by a plurality of sensors, it is possible to perform more advanced information analysis of a blood pressure waveform. For example, it is possible to classify pieces of data regarding blood pressure waveforms according to states of the user, such as a resting state and a moving state, a state when an atmospheric temperature is high and a state when it is low, a light sleep state and a deep sleep state, and so on. Alternatively, it is possible to extract information regarding the influence of body movement, an activity amount, activity intensity, a change in an atmospheric temperature, etc. on blood pressure, and thus evaluate the cause-effect relationship, the correlation, etc. between pieces of measurement data.

The processing unit 51 receives the indicators extracted by the indicator extraction unit 50. The processing unit 51 performs processing that is based on the received indicators. Various kinds of processing can be conceived of as processing that is based on the indicators. For example, the processing unit 51 may provide the values of the extracted indicators or changes in the values to a user, a doctor, a public health nurse, or the like to prompt the utilization of the indicators in the fields of health care, treatment, health guidance, and so on. Alternatively, the processing unit 51 may estimate respiratory risks from the extracted indicators, or present guidelines for health maintenance or risk mitigation. Furthermore, when an increase in a cardiovascular risk is detected or predicted based on an indicator, the processing unit 51 may inform the user or his/her doctor, or perform control to prevent the user from performing an action that places a burden on his/her heart and so on, or to prevent a cardiovascular event from occurring.

Information Acquired from Blood Pressure Waveform

Figure 6:
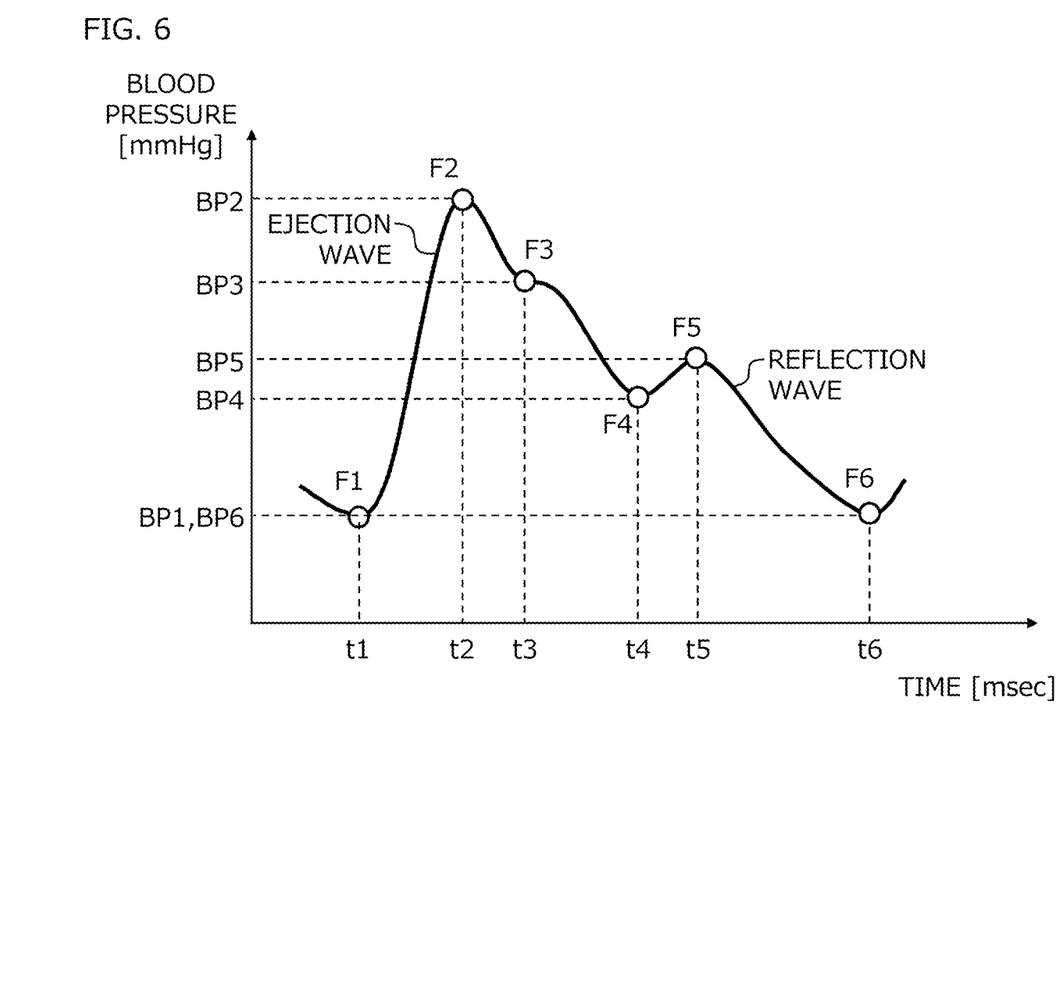
FIG. 6 shows a waveform (a blood pressure waveform) of a pressure pulse wave from a radial artery corresponding to one heartbeat.

FIG. 6 shows a waveform (a blood pressure waveform) of a pressure pulse wave from a radial artery corresponding to one heartbeat. The horizontal axis indicates time t (msec) and the vertical axis indicates blood pressure BP (mmHg).

A blood pressure waveform is the waveform of a composite wave constituted by an "ejection wave" that is generated when the heart contracts and pumps out blood, and a "reflection wave" that is generated when an ejection wave is reflected at a branch point of a peripheral vessel or an artery. The following shows examples of characteristic points that can be extracted from a blood pressure waveform corresponding to one heartbeat.

A point F1 is the rising point of the pressure pulse wave. The point F1 corresponds to the ejection start point of the heart, i.e. the point at which the aortic valve opens.

A point F2 is a point at which the amplitude (the pressure) of the ejection wave is at the maximum (a first peak).

A point F3 is an inflection point that appears midway in a drop in the ejection wave, due to a reflection wave being superimposed.

A point F4 is the minimum point, which appears between the ejection wave and the reflection wave, and is also referred to as a notch. This point corresponds to the point at which the aortic valve closes.

A point F5 is the peak of the reflection wave (a second peak), which appears after the point F4.

A point F6 is the end point of one heartbeat, and corresponds to the ejection start point of the next heartbeat, i.e. the start point of the next heartbeat.

The indicator extraction unit 50 may use any algorithm to detect the above-described characteristic points. For example, the indicator extraction unit 50 may perform computations to obtain an nth order differential waveform of a blood pressure waveform, and detect the zero-crossing points to extract the characteristic points (the inflection points) of the blood pressure waveform (the points F1, F2, F4, F5, and F6 can be detected from the first order differential waveform, and the point F3 can be detected from the second order differential waveform or the fourth order differential waveform). Alternatively, the indicator extraction unit 50 may read out, from the storage unit 27, a waveform pattern on which the characteristic points have been arranged in advance, and perform fitting of the waveform pattern to the target blood pressure waveform to specify the respective positions of the characteristic points.

The indicator extraction unit 50 performs computations based on time t and pressure BP of each of the above-described characteristic points F1 to F6, and can thus obtain various kinds of information (values, characteristic amounts, indicators, etc.) from the blood pressure waveform of one heartbeat. The following are typical examples of information that can be acquired from a blood pressure waveform. Note that tx and BPx respectively represent time and blood pressure corresponding to a characteristic point Fx.

Pulse Wave Interval (Period of Heartbeat) TA=t6−t1

Heart Rate PR=1/TA

Pulse Wave Rising Time UT=t2−t1

Systole TS=t4−t1

Diastole TD=t6−t4

Reflection Wave Delay Time=t3−t1

Maximum Blood Pressure (Systolic Blood Pressure) SBP=BP2

Minimum Blood Pressure (Diastolic Blood Pressure) DBP=BP1

Mean Blood Pressure MAP=(Area of Blood Pressure Waveform from t1 to t6)/Period of Heartbeat TA Mean Blood Pressure during Systole=(Area of Blood Pressure Waveform from t1 to t4)/Systole TS Mean Blood Pressure during Diastole=(Area of Blood Pressure Waveform from t4 to t6)/Diastole TD Pulse Pressure PP=Maximum Blood Pressure SBP−Minimum Blood Pressure DBP Late Systolic Pressure SBP2=BP3

AI (Augmentation Index)=(Late Systolic Pressure SBP2−Minimum Blood Pressure DBP)/Pulse Pressure PP Basic statistics of these pieces of information (values, characteristic amounts, and indicators) can also be used as indicators. Basic statistics include, for example, representative values (a mean value, a median value, a mode value, the maximum value, the minimum value, and so on) and the degree of scatter (dispersion, a standard deviation, a coefficient of variation, and so on). Temporal changes in these pieces of information (values, characteristic values, and indicators) can also be used as indicators.

In addition, the indicator extraction unit 50 can also acquire an indicator called BRS (Baroreflex Sensitivity) by performing computations on pieces of heartbeat information. This indicator indicates the ability to regulate blood pressure to be constant. Examples of methods for calculating the indicator include a spontaneous sequence method. This is a method for only extracting a sequence in which the maximum blood pressure SBP and the pulse wave interval TA consecutively rise or fall over the period of three or more heartbeats in synchronization with each other, plotting the maximum blood pressure SBP and the pulse wave interval TA onto a two-dimensional plane, and defining the inclination of the regression line obtained through a least squares method as the BRS.

As described above, the use of the biological information analysis system 10 according to the present embodiment makes it is possible to acquire various kinds of information from blood pressure waveform data. However, the biological information analysis system 10 need not implement all of the functions that are required to acquire all of the kinds of information described above. The biological information analysis system 10 need only implement functions that are required to acquire necessary information, depending on the configuration of the biological information analysis system 10, who the user is, the purpose of use, the location of use, and so on. Also, each function may be provided as a program module (a piece of application software), and the biological information analysis system 10 may employ a mechanism with which a function can be added by installing a necessary program module on the biological information analysis system 10.

The following illustrates an example, which is a specific application, of the biological information analysis system 10.

Example 1

The present example is an example in which, upon a surge in blood pressure being detected, whether or not the cause of the surge in blood pressure is apnea is determined, based on data regarding blood pressure waveforms. Specifically, the occurrence of apnea is detected by monitoring changes in systolic blood pressure based on time-series data regarding blood pressure waveforms.

In the present example, two pieces of information from among pieces of information that can be acquired from blood pressure waveforms, namely a systolic blood pressure and a heart rate (PR), are used. The method for calculating a systolic blood pressure (SBP) and a heart rate (PR) is as described with reference to FIG. 6, and information regarding a systolic blood pressure (SBP) and information regarding a heart rate (PR) can be acquired for each heartbeat from data regarding blood pressure waveforms.

Regarding changes in blood pressure caused by normal breathing, systolic blood pressure increases at exhalation (when a breath is let out), whereas the heart rate decreases. In contrast, regarding changes in blood pressure caused by sleep apnea, both the systolic blood pressure and the heart rate sharply increase at the end of sleep apnea (an arousal response), due to the enhanced activity of the sympathetic nerve system or the like. Therefore, it is possible to determine whether the cause of a change in blood pressure is sleep apnea or normal breathing, based on the relationship between: an increase and a decrease in the heart rate; and an increase and a decrease in systolic blood pressure. In the following description, a surge in blood pressure caused by sleep apnea is referred to as an "apnea surge".

Figure 7:
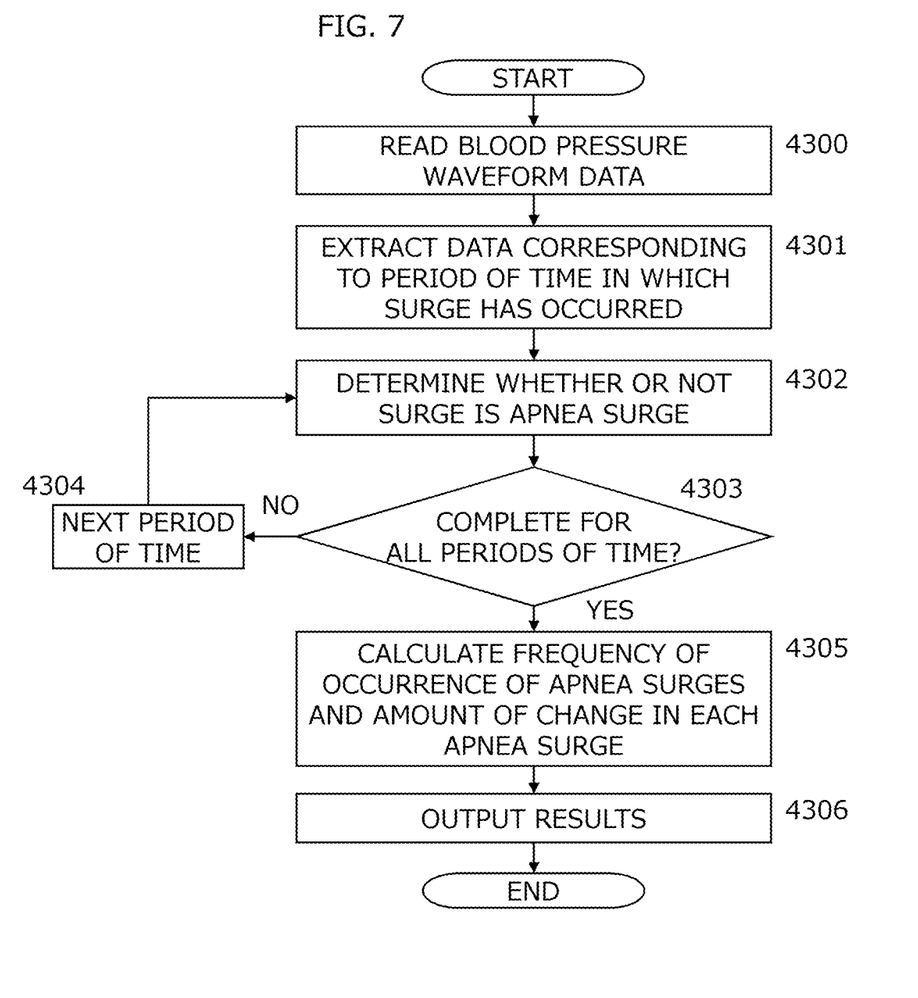
FIG. 7 is a flowchart for apnea surge determination processing according to Example 1.

FIG. 7 shows an example of a flowchart for processing according to the present example. First, the indicator extraction unit 50 reads data regarding blood pressure waveforms from the storage unit 27 (step 4300). For example, time-series data acquired overnight is read. The indicator extraction unit 50 detects a period of time in which a surge in blood pressure has occurred, from the time-series data regarding blood pressure waveforms, and extracts data regarding blood pressure waveforms corresponding to the period of time (step 4301). For example, the indicator extraction unit 50 may evaluate changes in systolic blood pressure for each period of time that corresponds to ten beats, and if an increase by no less than 10 mmHg from the initial value of systolic blood pressure is found in a period of time, the indicator extraction unit 50 may determine the period of time as an occurrence period in which a surge in blood pressure has occurred.

Figure 8:
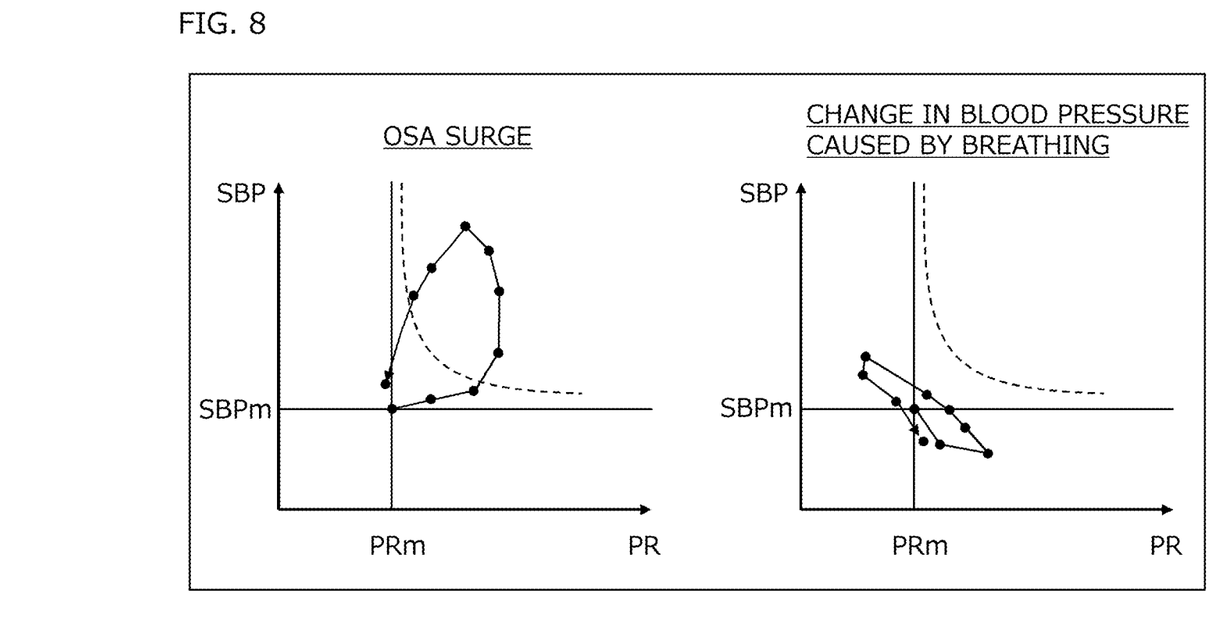
FIG. 8 is a diagram showing a logic for apnea surge determination according to Example 1.

Next, the indicator extraction unit 50 evaluates the relationship between: an increase and a decrease in the heart rate; and an increase and a decrease in systolic blood pressure for each of the occurrence periods extracted in step 4301, and determines whether or not the surge is an apnea surge (step 4302). FIG. 8 shows this logic for determination. In the charts shown in FIG. 8, the horizontal axis indicates the heart rate (PR), the vertical axis indicates the systolic blood pressure (SBP), where PRm denotes a reference heart rate, and SBPm denotes a reference systolic blood pressure. For example, representative values (a median value, a mean value, a mode value, etc.) in the period of one minute immediately followed by the surge occurrence period may be set as PRm and SBPm. The values of PRm and SBPm are stored in the storage unit 27 in advance, and the indicator extraction unit 50 may read and use the values of PRm and SBPm from the storage unit 27.

The dotted curved lines in the charts shown in FIG. 8 represent a determination condition that has been set with reference to the positions of PRm and SBPm. The indicator extraction unit 50 in the present example uses an inverse-proportional curve (a rectangular hyperbola) that is asymptotic to PRm and SBPm, as the boundary of the determination condition. Parameters for the determination condition (such as the constant of inverse proportionality) may be determined based on, for example, a medical mechanism or through machine learning using sample data. In the latter case, the following steps may be taken: (1) pieces of sample data regarding a surge in blood pressure are collected, and each piece of sample data is labeled so as to indicate whether or not the surge is an apnea surge, based on complex determination made by a doctor or the like; and (2) the determination condition is learned through machine learning, using a decision tree, logistic regression, discriminant analysis, an SVM, a neural net, or the like, based on the pieces of labeled data. In the present example, the boundary of the determination condition is an inverse-proportional curve. However, the boundary of the determination condition may be another kind of curved line, or a straight line, or a discontinuous boundary.

If pieces of data regarding a surge occurrence period corresponding to ten beats are plotted on a chart as shown in FIG. 8, a large number of data points are plotted on the upper right side of the determination condition in the case of an apnea surge, and a large number of data points are plotted on the lower left side of the determination condition in the case of a change in blood pressure caused by normal breathing. Therefore, for example, the indicator extraction unit 50 calculates a set of coordinate values on a chart for each piece of data corresponding to ten beats, determine, for each set of coordinate values, whether the set of coordinate values is located in the area on the upper right side of the determination condition, or in the area on the lower left side of the determination condition, and calculates the number or proportion of pieces of data located on the area on the upper right side of the determination condition. Thereafter, the indicator extraction unit 50 determine whether the surge in blood pressure in the occurrence period is a surge caused by apnea or a surge caused by another factor, based on whether or not the number or proportion of pieces of data located in the area on the upper right side of the determination condition is greater than a threshold value. The determination processing in step 4302 is performed on all of the surge occurrence periods detected in step 4301 (steps 4303 and 4304).

Next, the indicator extraction unit 50 calculates the frequency of occurrence of apnea surges and the amount of change in each apnea surge (step 4305). The frequency of occurrence is the number of surges in blood pressure that have occurred in a predetermined period of time (e.g. one day), and the amount of change is the difference between the reference value SBPm and the maximum SBP in each surge in blood pressure. The frequency of occurrence of, and the amount of changes in apnea surges can be used as indicators related to the functionality of respiratory organs or indicators indicating the respiratory event occurrence risk. The processing unit 51 provides information regarding the frequency of occurrence of, and the amount of changes in apnea surges, which have been acquired in step 4305, and information related to the functionality of respiratory organs, to the output unit 25 (step 4306). The processing unit 51 may provide a warning to the user when the frequency of occurrence of and/or the amount of changes in apnea surges is/are greater than a threshold value.

Figure 9:
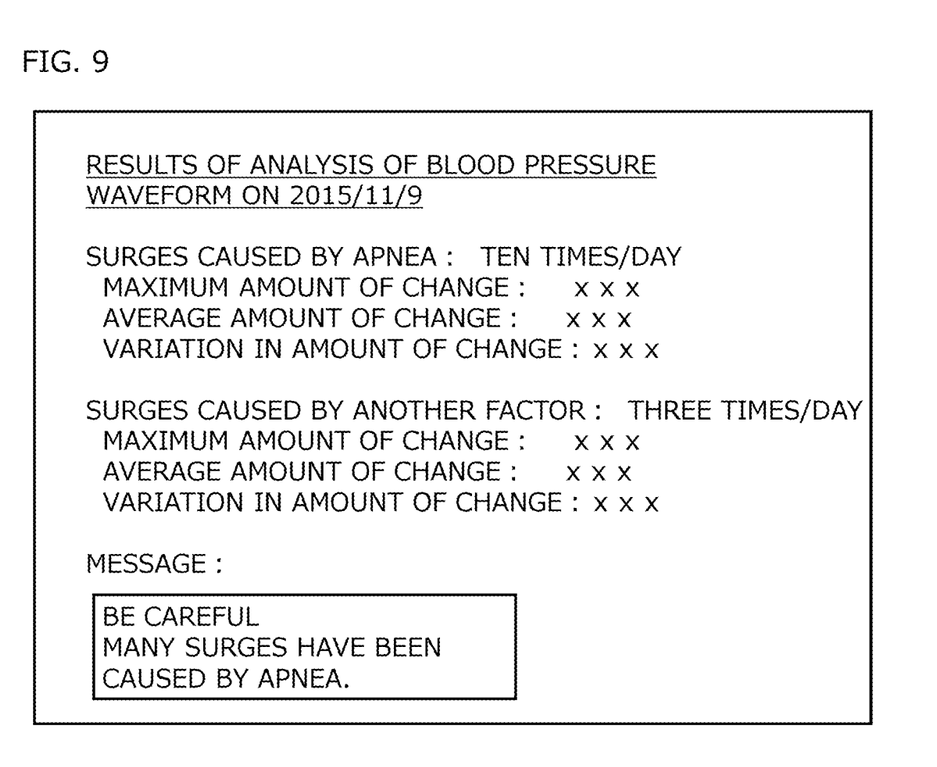
FIG. 9 shows an example of an information output screen according to Example 1.

FIG. 9 shows an example of an information output screen that is output by the output unit 25. In the example shown in FIG. 9, the frequency of occurrence per day and statistics (such as the maximum value, the mean value, and dispersion) of the amount of changes in surges in blood pressure are displayed for surges in blood pressure caused by apnea, and the frequency of occurrence per day and statistics of the amount of changes in surges in blood pressure are displayed for surges in blood pressure caused by a factor other than apnea. Furthermore, a message corresponding to the frequency of occurrence and the amount of changes (for example, a warning if apnea has occurred frequently) is also displayed.

With the above-described configuration, it is possible to determine whether the cause of a change in blood pressure is apnea or not by simply analyzing time-series data regarding blood pressure waveforms, and it is possible to use the results of analysis of blood pressure waveforms to evaluate the state of respiratory organs and the respiratory risk. Also, by comparing the frequency of occurrence of, and the amount of changes in apnea surges before and after medication, it is also possible to quantitatively evaluate the effect of medication.

The configurations according to the above-described embodiment and examples are no more than specific examples of configurations according to the present invention, and are not intended to limit the scope of the present invention. The present invention may employ various specific configurations without departing from the technical idea thereof.

The technical idea disclosed in the present description can be specified as the following aspects of the present invention.
Supplementary Note 1
A biological information analysis device comprising:
a hardware processor; and a memory that is configured to store a program,
wherein the hardware processor is configured to execute the program to
extract, from time-series data regarding blood pressure waveforms consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, and extract an indicator related to the functionality of respiratory organs of the user, based on characteristics of the blood pressure waveforms corresponding to the period of time, and
perform processing that is based on the indicator thus extracted.
Supplementary Note 2
A biological information analysis system comprising:
a sensor that is configured to be worn on a body part of a user and to be capable of non-invasively measuring a blood pressure waveform for each heartbeat; a hardware processor; and a memory that is configured to store a program,
wherein the hardware processor is configured to execute the program to
extract, from time-series data regarding blood pressure waveforms consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, and extract an indicator related to the functionality of respiratory organs of the user, based on characteristics of the blood pressure waveforms corresponding to the period of time, and
perform processing that is based on the indicator thus extracted.
Supplementary Note 3
A biological information analysis method comprising:
a step of acquiring, from time-series data regarding blood pressure waveforms that are consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, using at least one hardware processor;
a step of extracting an indicator related to the functionality of respiratory organs of the user, based on characteristics of the blood pressure waveforms corresponding to the period of time, using at least one hardware processor; and
a step of performing processing that is based on the indicator thus extracted, using at least one hardware processor.

INDEX TO THE REFERENCE NUMERALS

1 . . . biological information analysis device, 2 . . . measurement unit
10 . . . biological information analysis system, 11 . . . main body, 12 . . . belt
20 . . . blood pressure measurement unit, 21 . . . body movement measurement unit, 22 . . . environment measurement unit, 23 . . . control unit, 24 . . . input unit, 25 . . . output unit, 26 . . . communication unit, 27 . . . storage unit 30 . . . pressure sensor, 31 . . . pressurizing mechanism, 300 . . . pressure detection element 50 . . . indicator extraction unit, 51 . . . processing unit

The invention claimed is:

1. A biological information analysis device comprising:
at least one processor that operates as:
    an indicator extraction unit configured to extract, from time-series data regarding blood pressure waveforms consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, and extract an indicator related to the functionality of respiratory organs of the user, based on characteristics of the blood pressure waveforms corresponding to the period of time; and
    a processing unit configured to perform processing that is based on the indicator thus extracted; and
a display,
wherein the indicator extraction unit is configured to calculate a heart rate and a systolic blood pressure value for each of the blood pressure waveforms included in the period of time, using the data regarding the blood pressure waveforms corresponding to the period of time, and determine that a cause of a change in blood pressure in the period of time is apnea when the number or proportion of blood pressure waveforms in which both the heart rate and the systolic blood pressure value are greater than a predetermined determination condition is greater than a predetermined threshold value, and
wherein the processing unit is configured to output, on the display, information related to a change in blood pressure determined to be caused by apnea as the indicator related to the functionality of respiratory organs of the user.

2. The biological information analysis device according to claim 1, wherein the indicator extraction unit is configured to calculate the frequency of occurrence of changes in blood pressure caused by apnea, as the indicator related to the functionality of respiratory organs.

3. The biological information analysis device according to claim 1, wherein the indicator extraction unit is configured to calculate the amount and/or statistics of the amount of changes in blood pressure caused by apnea, as the indicator related to the functionality of respiratory organs.

4. A biological information analysis system comprising:
    a sensor that is configured to be worn on a body part of a user and to be capable of non-invasively measuring a blood pressure waveform for each heartbeat; and
    the biological information analysis device according to claim 1, the biological information analysis device being configured to analyze biological information, using data regarding blood pressure waveforms consecutively measured by the sensor.

5. A non-transitory computer-readable medium storing a program that causes a processor to function as the indicator extraction unit and the processing unit of the biological information analysis device according to claim 1.

6. A biological information analysis method comprising:
    a step of extracting, from time-series data regarding blood pressure waveforms consecutively measured by a sensor that is configured to be worn on a body part of a user and to be capable of non-invasively measuring a blood pressure waveform for each heartbeat, data regarding blood pressure waveforms corresponding to a period of time in which a change in blood pressure occurs, and extracting an indicator related to the functionality of respiratory organs of the user, based on characteristics of the blood pressure waveforms corresponding to the period of time; and
    a step of performing processing that is based on the indicator thus extracted,
wherein in the step of extracting, a heart rate and a systolic blood pressure value for each of the blood pressure waveforms included in the period of time are calculated, using the data regarding the blood pressure waveforms corresponding to the period of time, and it is determined that a cause of a change in blood pressure in the period of time is apnea based on the number or proportion of blood pressure waveforms in which both the heart rate and the systolic blood pressure value are greater than a predetermined determination condition being greater than a predetermined threshold value, and
wherein in the step of performing, information related to a change in blood pressure determined to be caused by apnea is outputted on a display as the indicator related to the functionality of respiratory organs of the user.

* * * * *